United States Patent
Krishnan et al.

(10) Patent No.: US 8,579,784 B2
(45) Date of Patent: *Nov. 12, 2013

(54) PERSONALIZED PROGNOSIS MODELING IN MEDICAL TREATMENT PLANNING

(75) Inventors: Sriram Krishnan, Exton, PA (US); R. Bharat Rao, Berwyn, PA (US); Christopher Jude Amies, Sykesville, MD (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 484 days.

This patent is subject to a terminal disclaimer.

(21) Appl. No.: 12/944,288

(22) Filed: Nov. 11, 2010

(65) Prior Publication Data

US 2011/0106749 A1   May 5, 2011

Related U.S. Application Data

(63) Continuation of application No. 11/735,720, filed on Apr. 16, 2007, now Pat. No. 7,844,560.

(60) Provisional application No. 60/792,450, filed on Apr. 17, 2006.

(51) Int. Cl.
*A61N 5/00* (2006.01)

(52) U.S. Cl.
USPC .......................................................... 600/1

(58) Field of Classification Search
USPC ..................... 600/1, 2; 128/897–899
See application file for complete search history.

(56) References Cited

U.S. PATENT DOCUMENTS

2005/0204264 A1   9/2005   Yusa
2006/0173663 A1*  8/2006   Langheier et al. .............. 703/11
2008/0301530 A1  12/2008   Spanel

FOREIGN PATENT DOCUMENTS

EP   1926102 A1   5/2008
EP   1927987 A2   6/2008

OTHER PUBLICATIONS

Stavrev P, Hristov D, Warkentin B, Sham E, Stavrena N, and Fallone BG. "Inverse Treatment Planning by Physically Constrained Minimization of a Biological Objective Function." Med. Phys. 30 (11) Nov. 2003. pp. 2948-2958.*
European Search Report dated Dec. 19, 2012 from corresponding EP Application No. 09843763.5.

* cited by examiner

*Primary Examiner* — Christine Matthews
*Assistant Examiner* — Joshua D Lannu
(74) *Attorney, Agent, or Firm* — Joshua B Ryan

(57) ABSTRACT

Automated treatment planning is provided with individual specific consideration. One or more prognosis models indicate survivability as a function of patient specific information for a given dose. By determining survivability for a plurality of doses, the biological model represented by survivability as a function of dose is determined from the specific patient. Similarly, the chances of complications or side effects are determined. The chance of survivability and chance of complication are used as or instead of the tumor control probability and normal tissue complications probability, respectively. The desired tumor dosage and tolerance dosage are selected as a function of the patient specific dose distributions. The selected dosages are input to an inverse treatment planning system for establishing radiation treatment parameters.

22 Claims, 5 Drawing Sheets

US 8,579,784 B2

PERSONALIZED PROGNOSIS MODELING IN MEDICAL TREATMENT PLANNING

RELATED APPLICATIONS

The present patent document is a continuation of U.S. patent application Ser. No. 11/735,720, filed Apr. 16, 2007, which claims the benefit of the filing date under 35 U.S.C. §119(e) of Provisional U.S. Patent Application Ser. No. 60/792,450, filed Apr. 17, 2006, all of which are hereby incorporated by reference.

BACKGROUND

The present embodiments relate to medical treatment planning. The goal of radiation treatment planning is to calculate a set of parameters to control a radiation therapy device for delivering radiation to a patient. Ideally, all of the radiation delivered is concentrated within a tumor, and no radiation is delivered outside the tumor. Practically, this is not likely. Therefore, radiation treatment planning attempts to find a solution that trades off radiation dose to the tumor and radiation dose outside the tumor.

A human operator may set the radiation treatment parameters, such as number of beams, beam location, beam direction, and beam strength. The predicted radiation dosages to the tumor and outside the tumor are computed from the operator set radiation treatment parameters. Inverse treatment planning systems (ITPS) have been developed that attempt to create an optimal solution of radiation treatment parameters given an objective function. This objective function measures how well a particular radiation plan meets the goals of the treatment.

The objective function is based either on dose or on a generic biological model. Objective functions based on dose require an input as to what the desired dose should be within a defined tumor, and what the desired dose should be outside the tumor. The ITPS then tries to optimize a solution to meet these criteria. Objective functions based on biological parameters include a generic model for how different dose distributions affect a tumor and how different dose distributions affect normal tissue outside the tumor. The input to the system is the desired tumor control probability (TCP) and normal tissue complications probability (NTCP). The system tries to maximize TCP and minimize NTCP to meet the desired goal. This is done by using the biological model to extract the desired dosage to the tumor, and allowed tolerances of dose to normal tissue, to achieve these TCP and NTCP goals. Given the dosages, the radiation treatment parameters are determined. However, the radiation treatment parameters may not be optimal for a given patient.

SUMMARY

In various embodiments, systems, methods, instructions, and computer readable media are provided for automated treatment planning with individual specific consideration. One or more prognosis models indicate survivability as a function of patient specific information for a given dose. By determining survivability for a plurality of doses, the biological model represented by survivability as a function of dose is determined for the specific patient. Similarly, the chances of complications or side effects are determined. The chance of survivability and chance of complication are used as or instead of the tumor control probability and normal tissue complications probability, respectively. The desired tumor dosage and tolerance dosage are selected as a function of the patient specific dose distributions. The selected dosages are input to an inverse treatment planning system for establishing radiation treatment parameters.

In a first aspect, a system is provided for automated treatment planning with individual specific consideration. An input is operable to receive values for a plurality of patient specific characteristics of a patient. A processor is operable to apply the values to a first prognosis model. The first prognosis model relates a plurality of variables corresponding to the values to a first probability at a given dose. The processor is operable to provide a first input to an inverse treatment planning system where the first input being a function of the first probability. A display is operable to output radiation treatment parameters provided by the inverse treatment planning system as a function of the first probability.

In a second aspect, a computer readable storage medium has stored therein data representing instructions executable by a programmed processor for automated treatment planning with individual specific consideration. The instructions include: determining a first dose distribution of chance of survival as a function of dose, the first dose distribution output by a prognosis model as a function of first values specific to an individual patient; determining a second dose distribution of chance of complication as a function of dose, the second dose distribution output by the prognosis model as a function of second values specific to the individual patient; selecting a tumor dose from the first dose distribution corresponding to a desired chance of survival; selecting a dose tolerance from the second dose distribution corresponding to a desired chance of complication; and determining a radiation treatment plan as a function of the tumor dose and the dose tolerance.

In a third aspect, a method is provided for automated treatment planning with individual specific consideration. Patient specific values are applied to a prognostic model. A probability of survival is output from the prognostic model in response to the applying. A first dose is input, as a function of the probability of survival, to an inverse treatment planning system. A radiation treatment plan is output from the inverse treatment planning system in response to the first dose.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

Figure 1:
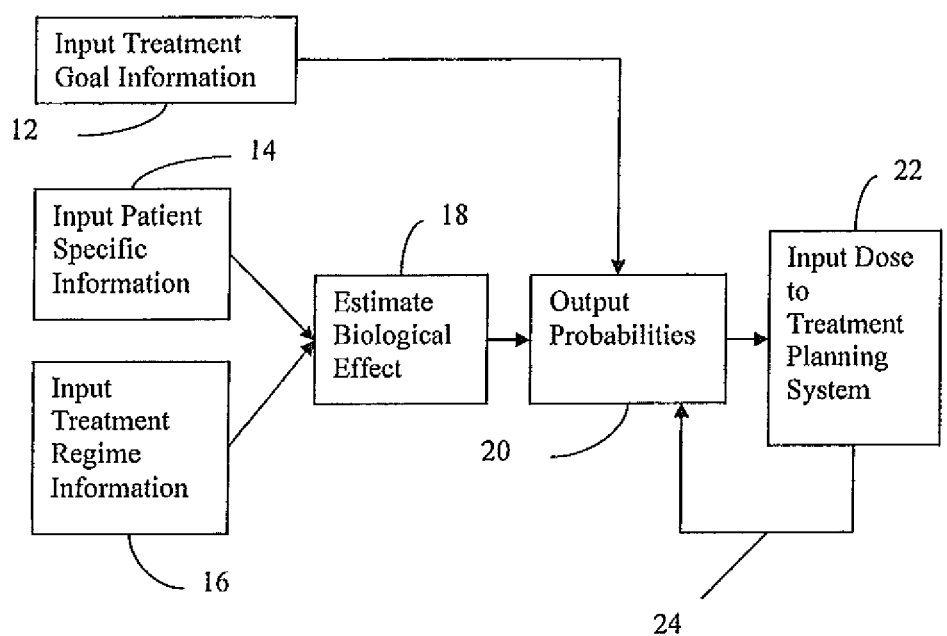
FIG. 1 is a flow chart diagram of one embodiment of a method for individualized treatment planning.

Treatment planning for radiation therapy uses patient specific information. TCP and NTCP models are based on generic models, from either clinical trials or other sources of medical knowledge. However, each individual may have a unique TCP or NTCP curves for dose distributions. By tuning the TCP or NTCP models to a particular individual, an optimum treatment may result. These biological models are modified based on individual and/or treatment characteristics to individualize the TCP and NTCP models. The resulting dosages and allowed tolerances input to the ITPS systems may more likely reflect dosages appropriate for an individual patient. The ITPS outputs a predicted dose to the tumor and normal tissue achievable by the radiation therapy system.

The individualization of the biological models may be constructed in several ways. One approach is to construct careful trials where patient data is collected on large numbers of patients, and then dosages and outcomes are measured. The outcomes are then correlated back to the dosages and patient data to come up with a model for how outcomes are determined by individual patient data. However, this approach may be expensive, as the number of different patients required would be very large to account for both variations in dosages and patient data.

In an alternative approach, a prognosis model predicts outcomes (e.g. survival) and side effects (e.g. disease) based on patient specific values. The output as a function of dose provides the biological curves. For example, the prognosis model is derived from literature and/or a database, such as disclosed in U.S. patent application Ser. No. 11/735,736, filed on the same day as the parent application), the disclosure of which is incorporated herein by reference. The prognosis model is used as the biological model for dosage distribution. The chance of survival and/or chance of complication may be derived by modeling with a fewer number of patient records than data intensive trials. The chance of survival and chance of complication are used as the tumor control probability and the normal tissue complication probability in an inverse treatment planning system.

Any prognosis model may be used. In one embodiment, a model derived from published literature is used. Published literature is an available source of reliable information for modeling even where large databases are not available. For increased accuracy, treatment outcome (e.g., survivability and complication) is predicted from statistical models that combine several sources of data, such as literature and data driven models. For example, 2-year survival of non-small-cell lung-cancer (NSCLC) patients is predicted based on individual or patient specific information. The prediction uses knowledge base gleaned from literature and a database. By incorporating both sources of information into a combined model, consistency and accuracy of the predictions may be improved.

The automated treatment planning may be associated with a healthcare workflow. For example, patient data mining or manual input provides values to one or more prognosis models. The values are for a particular patient. The model or models generate a probability regarding a possible treatment based on the values. The model or models may perform the prognosis iteratively to determine an optimal treatment, such as modeling different treatment possibilities. Alternatively, the suggested treatment is input and the prognosis associated with the treatment is output. A dose associated with a desired combination of probability of survivability and a tolerable probability of complications is selected based on the individualized prognosis. The dosage and tolerance are output to an inverse treatment planning system (ITPS). The ITPS and prognosis model or dose distributions determined by the prognosis model may be used iteratively to optimize an achievable treatment plan. The prognosis model may account for other treatments, such as chemotherapy, surgery, and/or fractionation, to provide a treatment regime for the individual patient. Any now known or later developed software or system providing a workflow engine may be configured to automate treatment planning with consideration for specific patient attributes.

Figure 2:
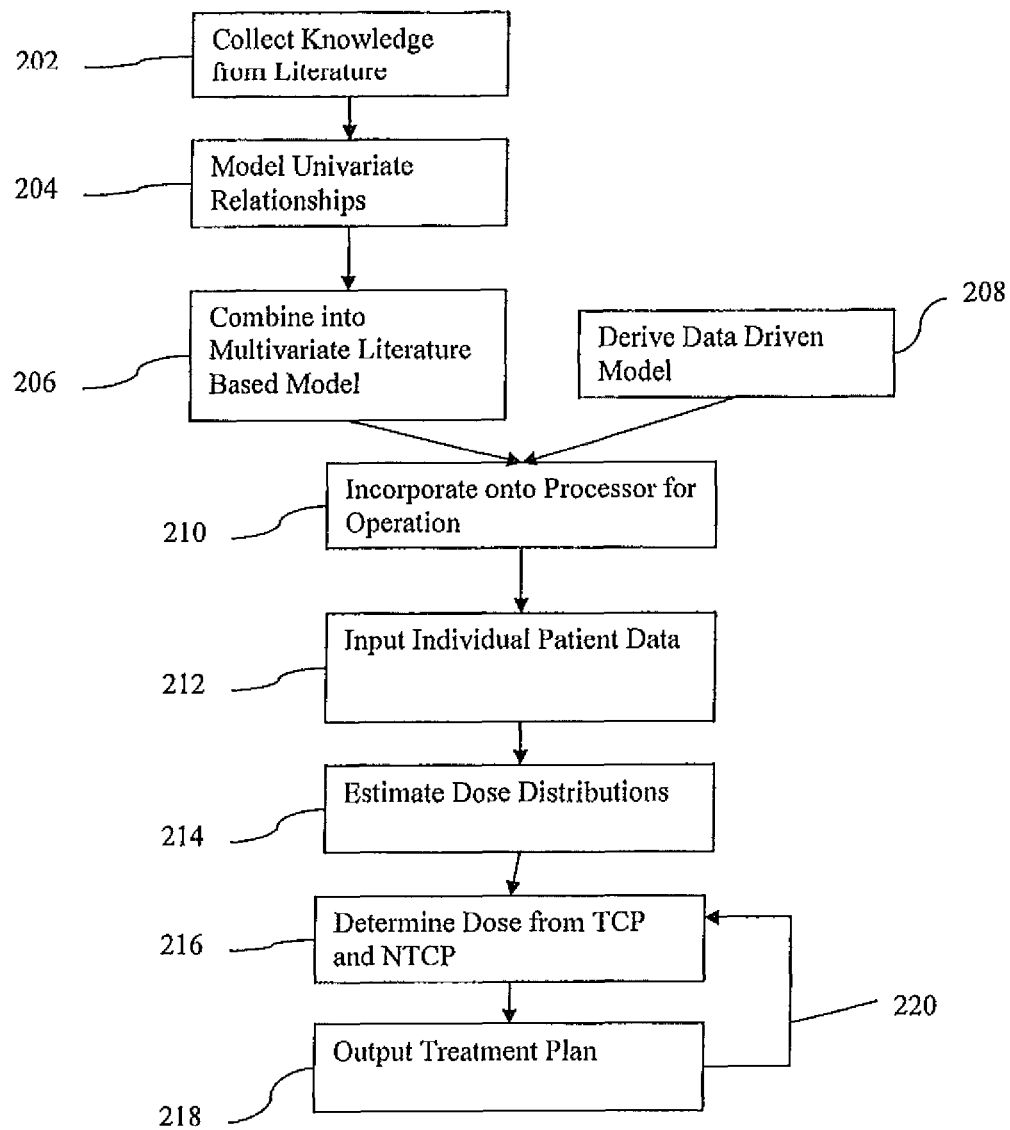
FIG. 2 is a flow chart diagram of another embodiment of a method for individualized treatment planning.

FIGS. 1 and 2 show embodiments of a method for automated treatment planning with individual specific consideration. The method is implemented with the system of FIG. 3 or a different system. The acts are performed in the order shown or a different order. Additional, different, or fewer acts may be provided. For example, acts 202-210 of FIG. 2 are not provided. FIG. 1 shows use of patient specific values for determining a treatment plan. FIG. 2 shows the development of one embodiment of a prognosis model and subsequent use for determining a treatment plan.

Referring to FIG. 2, in act 202, quantitative medical knowledge of predictors for a disease is collected from literature. The literature is any published information, preferably credible. The literature sources may be books, medical journals, theses, reports, or other publications. One or more literature sources are used. For example, the leading or many publications associated with a particular disease and different treatment options are used. The literature may report the results of clinical studies.

The knowledge is collected for a specific disease or a group of related diseases. The knowledge reflects survivability and side effects (complications) associated with one or more treatments, such as different doses of a same type of treatment. The reported outcomes and corresponding treatments associated with a disease are collected.

Any indication of a variable's correlation with outcome may be collected. The quantitative medical knowledge may be provided as a table, a graph, text, or combinations thereof. For example, the characteristics of the patient population targeted, the overall survival rates of the patient population, the survival rates of certain sub-populations exhibiting certain characteristics, the hazard ratio, fraction of patients in a study receiving treatment, grouping information, treatment, outcome, or other quantities are collected. Typically, the literature reports a study with two groups of patients, one group receiving a treatment and another group not receiving the treatment. The fraction of the patients between the two groups at the start of the study, the overall survival rate after a period, and the hazard ratio are given. In other publications, different, additional, or less information is provided. Values not reported directly may be inferred from the information provided in the literature, possibly requiring additional assumptions to make up for missing pieces of information.

The collection is performed manually. For example, one or more people review the literature and enter the information into a database or spread sheet. The collecting, review of the collection, or selection of sources to be used for collecting may be performed or reviewed by a doctor or other knowledgeable source. In an alternative embodiment, the information is collected automatically or semi-automatically. For example, the data mining discussed below is used to mine free text, other unstructured sources, or structured literature sources to collect the desired information. Combinations of manual and automatic collection may be performed.

In act 204, the relationship between the patient information and outcomes is determined. In one embodiment, a multivariate model is created from the collected information without determining individual relationships. In another embodiment, univariate relationships between a dose and different predictors (i.e., different patient information variables correlated with an outcome) are separately modeled from the quantitative medical knowledge. The statistical model and parameters underlying the reported results of the literature are reverse engineered from the collected data.

In one example embodiment, the literature includes a graph showing the outcome as a function of a variable. For example, the chance of surviving two years as a function of amount of smoking may be provided for a given treatment. By fitting a curve to the graph, a mathematical representation of the graph is provided for computer use. Linear, quadratic, or other fitting may be used. Alternatively, logic corresponding to the graph (e.g., if-then statements) models the graph.

In another example embodiment, the literature includes a table showing outcome as a function of the variable. The table is converted into logic statements for use by a computer. Alternatively, the table is used as data points for curve fitting. The fit curve models the table.

In yet another example embodiment, a binary classification is determined with a logistic or Cox regression. The classification is determined from a table, graph, text, or combinations thereof. Other modeling or classifications may be used. In other embodiments, a combination of models is determined for a univariate relationship, such as using both classification and curve fitting. Two different models represent the same relationship.

As an example of classification, an overall survival rate ($S_{av}$), a hazard ratio (h), and a fraction of study patients associated with different binary values (P=0 and P=1) of a variable being studied for correlation with outcome are collected and used for modeling one univariate relationship. The survival rate of each separate group of the patients may not be provided separately, so is modeled. For example, an overall survival rate is provided, but the separate survival rates for each of the two groups of patients are not provided. The separate survival rates are modeled.

Using a Cox regression model example for the binary predictor P, the collected data is classified. The value of the hazard ratio may be given as: $h=H_{P=0}/H_{P=1}$. The fraction of patients with P=0 and P=1 may be denoted by $w_{P=0}$ and $w_{P=1}$. The probability of 2-year survival for the sub-populations, denoted by $S_{P=0}$ and $S_{P=1}$, with P=0 and P=1 is inferred. The fraction is known at time zero (the beginning of the study), but not at the end of the study. An exponential, Weibull, or other distribution of the survival times is assumed or known. For an exponential decline, the equation: $w_{P=0}S_{P=1}^{h}+w_{P=1}S_{P=1}=S_{av}$ results. This equation includes the hazard ratio as an exponential term, the relative fractions as weights, the overall survival rate, and the desired two-year survival of one group of patients. The equation is solved (numerically) for $S_{P=1}$. The relationship of the two-year survival of the other group of patients is represented as; $S_{P=0}=(S_{av}-w_{P=1}S_{P=1})/w_{P=0}$ The results are probabilities of survival after two years for the binary predictor (variable).

In the example above, a specific regression model was used. Other models may be used, such as logistic regression. The outcome modeled in the example is survivability, but other outcomes may be modeled, such as complications. The two-year survival was modeled, but other terms may be used. A range of times (e.g., 4-10 year survival) may be interpolated or extrapolated for a given predictor. Other equations may be used. Other quantities may be used. Non-binary modeling may be used. Other literature sources may give different types of information, so the modeling may be different based on context.

Different variable's relationship with outcome for a given treatment may be modeled. For example, portions of the prognosis model may provide outcome for a given dose as a function of the input variables. Different or the same modeling may be used. Any variable may be used, but statistically significant variables are preferred. Where available or desired, additional univariate relationships are modeled for a given treatment.

In act 206, the models for the univariate relationships are combined into a multivariate model. Any combination may be used. Since the relationships reflect probabilities, the combination may be probabilistic. For example, suppose a lung cancer patient has a 30% probability of two-year survival on average; and a smoker with lung cancer has a 27% probability of two-year survival, while a non-smoker with lung cancer has a 40% probability; moreover, suppose men with lung cancer have a 25% probability of two-year survival, while women have a 35% chance. Assuming that the gender of the patients and their smoking habits are independent of each other (which may not be true in practice), one can combine these two predictors, and obtain, for instance, that a non-smoking woman has a 45.6% chance of two-year survival, while a smoking man has a 22.3% probability of two-year survival.

As another possible combination, a Bayesian network is formed as the multivariate model from the univariate relationships. Bayesian networks serve as multivariate quantitative models that capture medical knowledge in the form of (probabilistic) causal effects. Other networks or combined models may be used.

The combination assumes the various univariate prediction models are independent of each other. Alternatively, the relationship between univariate prediction models is known or determined and included as part of the combination.

Apart from the literature, information obtained from physicians may be included in the literature model. The physician's knowledge may provide reasonable assumptions for filling in information missing in the literature or relationship between variables for forming the multivariate model. Other sources of information, such as derived from a database of patient records, may also be included, or maintained separately as a different prognosis model.

The modeling and combination of acts 204 and 206 are performed by a computer or manually. The model may be developed with the aid of a computer. The modeling and combination are programmed so that a computer may apply the resulting model to data for individual patients.

In optional, additional, or alternative act 208, a data driven model is derived. Any now known or later developed data driven model may be created, such as a linear discriminant analysis, relevance vector machine, or by data mining as disclosed in U.S. Patent Application Publication No. 2003/0126101, the disclosure of which is incorporated herein by reference. Medical records for a plurality of patients are processed to model variables to outcome for one or more doses, treatments, and/or treatment regimes. By mining or processing a database of patient information from previously treated patients, a model of values' relationships to outcome is developed by a computer.

No, one, two or more data driven models may be derived. In one example for NSCLC patients, two models are derived. One model is derived with a linear discriminant analysis. The predictors in this logistic-regression model are chosen based on the literature, but may be selected from data analysis or by a physician. The model parameters are derived from the data available from an institution database of a plurality of previous patients. The other model is derived in a data-driven way using a relevance vector machine. The relevant predictors and the model parameters are both determined by the model or data processing.

The knowledge base used for each model is different or the same. For example, the multivariate model of act 206 is based on literature with or without physician provided information. The models in the example for act 208 above are based on a same database. The literature driven model may be used as prior medical knowledge when learning the data driven model from the patient data. The prior medical knowledge is incorporated into machine learning from the database. The medical knowledge may be weighed against the information from the patient data for validation.

The model creation acts may be repeated for different dosages, types of treatment, and/or complications. An array of models may be provided in the prognosis model in order to explore the possible outcomes associated with different options for a same patient.

In act 210, the models are incorporated onto a computer, such as into hardware, software, or both. The incorporation allows operating, with a processor, combined models or a single model as a prognosis model for an individual patient. Values for the predictors of the models are obtained. The medical record or other source provides values for a specific or individual patient. The model is applied to the individual patient information. One or more, such as both the data driven model and the literature driven model from acts 206 and 208, are applied as the prognosis model.

Separate outputs from the different models may be provided. Alternatively, the models are incorporated to provide a single output or related outputs. The combined model may be an improved prediction-model based on multiple sources of information. Regardless of the format of the output, one or more separate or combined models perform as a prognosis model.

Any combination may be used. In one embodiment, the models are combined as an ensemble. The prediction of the different models is combined, such as a weighted average or majority vote. Different models may use different predictors or variables for input. If the models to be combined have the same input variables or predictors, then the models may be fused. The models are combined to form a single model, such as a Bayesian network.

In act 212, individual patient data is input for application of the prognosis model. The patient specific values input corresponds to the predictors or variables used by the models. Where a value for an individual patient is not available, a value may be assumed, such as using an average, or left blank.

Any now known or later developed variable correlating with outcome may be input. For example, the values may be for clinical data about the patient, such as age, history (e.g. nicotine use for lung cancer), lung function, gender, and/or activity level. As another example, the values may be for genomic and proteomic variables. Referring to FIG. 1, act 14 shows the input of patient specific information.

In FIG. 1, act 16 shows input of treatment parameters, such as fractionation of dosages, overall treatment time, concurrent chemotherapy, or other variables for treatment regime. This information includes the proposed treatment plan for the individual. The prognosis model may include indication of increased or decreased likelihood of survivability or complication given previous performance of other treatments. Different individuals may react differently to different treatment parameters.

The data is input manually. Alternatively, the data is mined from a structured database. If values are available from unstructured data, the values may be mined by searching or probabilistic inference. A processor mines the values from a medical record of the individual patient. For example, the mining discussed below is performed. The mined and/or manually input values are applied to the combined models to obtain an outcome prediction, such as a survival rate for a treatment of the individual patient.

In act 18 of FIG. 1, the biological effect of dose is estimated based on the patient specific values. The estimation is performed by applying the values for a patient to the prognosis model. The prognosis model determines an outcome, such as one or more probabilities, as a function of the applied values. The prognosis model determines the outcome using knowledge base from one or more sources, such as from clinical study publications, other literature, and/or a database.

In the embodiment of FIG. 2, the biological effect is determined in act 214. The biological effect is determined as one or more dose distributions, such as two dose distributions. In one embodiment, the biological effect is determined as a dose distribution of probability of survival as a function of dose. The prognosis model provides two or more outcomes associated with two or more possible doses. One possible dose may be no additional radiation or lack of treatment. The prognosis model estimates a range of probabilities for a range of doses. Other values in the distribution may be interpolated or extrapolated. The dose distribution represents the probability of survival given different doses in treatment based on patient specific information, such as the size of the tumor, age, nicotine use, lung function, gender, activity level and/or other variables.

In another embodiment, the biological effect is determined, by the prognosis model, as the dose distribution of probability of complication as a function of dose. The same or different values are applied to the same or different part of the prognosis model. The prognosis model provides two or more outcomes associated with two or more possible dose. One possible dose may be no additional radiation or lack of treatment. The prognosis model estimates a range of probabilities for a range of doses. Other values in the distribution may be interpolated or extrapolated. The dose distribution represents the probability of complication given different doses in treatment based on patient specific information. In one embodiment, the dose distribution is of dose to the tumor. In another embodiment, the dose distribution is of dose to normal tissue.

In act 214, the treatment outcome is predicted with the literature-based model. The prognosis model may predict outcome with another model. The same or different data for the individual patient is input. The other model is based on a different source of information, such as a data driven model. The model operates as a function of model parameters with a database of past patient information for a plurality of patients as a knowledge base source. A unified, combined or single outcome is estimated from the different models of the prognosis model.

The treatment outcome is based on a dose of radiation given the patient specific information. The treatment outcome may be a function of other possible treatments, such as chemotherapy, type of drug, amount of drug, surgery, radiation timing (e.g., fractionation), or other treatment, or treatment combination. The literature-based model is derived from quantities in clinical study publications as a knowledge base source. The patient specific information is input to the model as values for variables identified from the literature. The application results in one or more predicted treatment outcomes, including probability of survival as a function of treatment regime and/or radiation dose.

In act 20 of FIG. 1, one or more probabilities of survival are output from the prognostic model. The probabilities may be output as a table, distribution, or single value. In one embodiment, a dose distribution of probabilities of survival as a function of dose and/or treatment regime is output. One or more probabilities of complications are output in addition or alternatively. Other probabilities may be output, such as probabilities as a function of dose and other treatment or as a function of treatment regime.

The output is provided in response to applying the patient specific values. Based on the values for a given patient, the biological effect of radiation treatment is estimated and output for the specific patient. The output may be different for different patients due to differences in the medical record, medical history, or patients.

The output is used to determine a dose for input to a treatment planning system. The dose to be applied to the tumor and the acceptable dose to tissue outside the tumor are selected as a function of the probabilities. The selection is based, in part, on the treatment goals.

In act 12, treatment goals are input. The treatment goals are input manually, such as by a physician or patient. Alternatively, the treatment goals are determined by a processor, such as based on likely goals, a common goal, or other information.

The treatment goals may include a chance of survival and a chance of complication. For example, a 70% chance of survival with only 5% chance of complications is desired. Other treatment goals may be provided, such as no chemotherapy or other treatment regime limitations.

As indicated at act 216 of FIG. 2, the dose is determined from the tumor control probability and the normal tissue complication probability. In one example, the probability of survival is used as the tumor control probability, and the probability of complication is used as the normal tissue complication probability.

The dose associated with the desired probability is selected. For example, the dose associated with a chance of survival equal to or better than a treatment goal is selected. Given the selected dosage, the probability of complication is examined. If the probability of complication is below the corresponding treatment goal, a range of dosage greater than the selected dosage up to the complication treatment goal may be provided. For example, 60 Gy of tumor dosage may provide 70% chance of survival, and 3% chance of complication. Up to 65 Gy may still provide 5% or less chance of complication based on the dose distribution for complication. A 5 Gy tolerance for complication is determined. In other embodiments, the initial selection of dose is based on complications with a tolerance given based on the survivability. The dose (e.g., 60 Gy) is selected as a function of both complication and survival distributions. The dose distributions are related to each other by the dose being examined.

In another example, one of the treatment goals does not allow for another treatment goal. For example, 1% complication is desired, but the associated dose may only provide a 40% chance of survival where a 70% chance is desired. Feedback may be provided to the user to select different goals. The feedback may include the dose distributions. The user may select the treatment goals based on the dose distributions. The feedback may include a computer-based output of possible treatment goals given the dose distributions. A range of options may be output.

Other selections and associated criteria may be used. As another example, the tumor dosage (e.g., 60 Gy) for the individual patient to provide the desired goal is selected. The normal tissue dosage (e.g., 5 Gy) for the individual patient to provide the desired limit on tissue exposure is selected. The selection is based on the dose distribution provided by the prognosis model for the specific patient values.

In act 22 of FIG. 1, the selected tumor dose and normal tissue dose, selected dose and associated tolerance, selected probabilities of survival and complication, or other information are input to the inverse treatment planning system. The dose is provided in Gy or other type of value. The tolerance dose is provided in Gy, a percentage of the tumor dose, or other type of value. The location and dimensions of the tumor to be treated are also input.

The inverse treatment planning system determines treatment parameters for the input information. For example, the number of beams, beam location, beam direction, beam strength, and/or other treatment parameters achievable by the therapy device to provide the desired amount of tumor dose and not exceed the desired amount of normal tissue dose is determined. Since the focus of the beams is not a point and the radiation passes through normal tissue to reach the tumor, normal tissue is exposed for the treatment plan. The combination of treatment parameters optimizes the treatment to limit normal tissue dose and maximize tumor dose.

In act 218 (FIG. 2), the radiation treatment plan or parameters are output. In response to the input tumor dose and/or normal tissue dose, parameters are provided to guide the radiation therapy. The parameters may be optimized for one or more dosages, such as providing the maximum tumor dose within the normal tissue tolerance, minimizing the normal tissue dose while achieving the tumor dose, or a combination thereof.

If the therapy system is incapable of providing the tumor dose given the limitation on normal tissue dose, the process may feedback in acts 24 of FIG. 1 and/or act 220 of FIG. 2. The feedback aids determination of a different dose in act 216 of FIG. 2 or different use of the output of probabilities in act 20 of FIG. 1.

The feedback may include options, such as the normal tissue dose resulting from meeting the tumor dose and/or vise versa. Achievable tumor and/or tolerance dose are provided. The results may be sent to the user with an alert that the desired goals could not be achieved.

The dose distributions are used to determine other possible dosages that may be achievable. If these dosages are not within the specifications desired, the values can be sent back to the model, and the predicted survivability and complication probabilities, and consequently the predicted outcome (longetivity, side effects, etc) are computed for the real or achievable doses.

The feedback may be provided even where the treatment plan satisfies the tumor dose and the normal tissue tolerance. The radiation treatment plan may be optimized as a function of the achievable tumor dose, the achievable tolerance dose, and the first and second dose distributions. Using the dose distributions and a priority on tumor dose, normal tissue dose, other priority, or a combination thereof, the treatment plan may be altered. For example, the achievable tumor dose is greater given the normal tissue tolerance. The dose distribution may provide a greater chance of survival for an increased dose. If so, the increased dose may be used. If not, the lesser tumor dose with resulting lesser chance of complication may be maintained. Differences in the relationship of dose to complication and survivability may allow optimization based on desired priorities. Iterative probability and dose selection with treatment planning may be used.

In one embodiment, the prognosis model is used to select a treatment regime. The simultaneous optimization of a treatment regime with radiation planning may lead to a more optimal overall treatment plan, and hence outcome. The prognosis model indicates survivability and/or complication as a function of patient specific values. The prognosis model includes different portions associated with different treatment regimes. The treatment regime with the highest probability of survival, least chance of complication, or a combination of higher probability of survival and lower probability of complication is selected. The patient specific values are used to predict the optimum treatment regime for a patient. The treatment regime may provide for chemotherapy, surgery, hormone therapy, other therapy, and/or radiation treatment. Considerations that are more complex may be included in the treatment regime, such as type of drug for chemotherapy, treatment time, type of radiation, type of radiation therapy, and/or fractionation of radiation treatment. If the treatment regime includes radiation therapy, the radiation treatment parameters are determined.

Once treatment has actually begun, the treatment planning process may be repeated. The actual dose delivered and/or measured may be an input value for the prognosis model. The predicted outcomes of probability of survivability (e.g., used as TCP) and probability of complication (e.g., used as NTCP) may be computed using the modified biological model (i.e., prognosis model), and presented to the physician. New treatment parameters may be determined to account for differences from planned treatment and/or changes in the patient condition.

Figure 3:
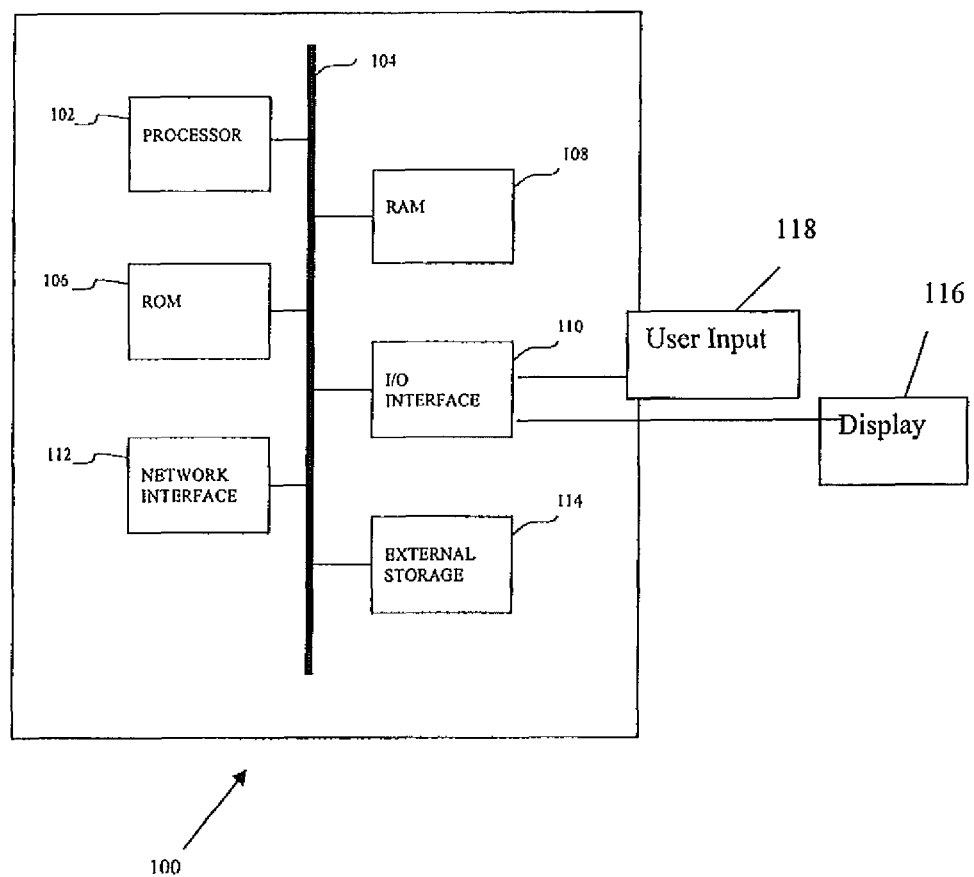
FIG. 3 is a block diagram of one embodiment of a system for applying a prognosis model in radiation treatment planning.

FIG. 3 shows a block diagram of an example system 100 for automated treatment planning with individual specific consideration. The system 100 is shown as a hardware device, but may be implemented in various forms of hardware, software, firmware, special purpose processors, or a combination thereof. Some embodiments are implemented in software as a program tangibly embodied on a program storage device. By implementing with a system or program, semi-automated or automated workflows are provided to assist a user in generating a radiation treatment plan.

The system 100 is a computer, personal computer, server, PACs workstation, imaging system, medical system, network processor, network, or other now know or later developed processing system. The system 100 includes at least one processor 102 operatively coupled to other components via a system bus 104. The processor 102 is implemented on a computer platform having hardware components in one embodiment. The computer platform also includes an operating system and microinstruction code. The various processes, methods, acts, and functions described herein may be either part of the microinstruction code or part of a program (or combination thereof) which is executed via the operating system.

The other components include memories (ROM 106 and/or RAM 108), a network interface 112, an external storage 114, an input/output interface 110, a display 116, and the user input 118. Additional, different, or fewer components may be provided.

The user input 118, network interface 112, or external storage 114 may operate as an input operable to receive values for a plurality of patient specific characteristics of a patient. The values are for variables to be used by one or more models. The values may be manually input and/or input by a processor, such as inputting data as part of mining from a database in the external storage 114 or elsewhere.

The user input 118 is a mouse, keyboard, track ball, touch screen, joystick, touch pad, buttons, knobs, sliders, combinations thereof, or other now known or later developed input device. The user input 118 operates as part of a user interface. For example, one or more buttons are displayed on the display 116. The user input 118 is used to control a pointer for selection and activation of the functions associated with the buttons. Alternatively, hard coded or fixed buttons may be used.

The network interface 112 may be a hard-wired interface. However, in various exemplary embodiments, the network interface 112 may include any device suitable to transmit information to and from another device, such as a universal asynchronous receiver/transmitter (UART), a parallel digital interface, a software interface or any combination of known or later developed software and hardware. The network interface 112 may be linked to various types of networks, including a local area network (LAN), a wide area network (WAN), an intranet, a virtual private network (VPN), and the Internet. The processor 102 or network interface 112 provides a data interface operable to receive values mined from data by the processor 102 or a different processor.

The processor 102 has any suitable architecture, such as a general processor, central processing unit, digital signal processor, application specific integrated circuit, field programmable gate array, digital circuit, analog circuit, combinations thereof, or any other now known or later developed device for processing data. The processor 102 may be a single device or include multiple devices in a distributed arrangement for parallel and/or serial processing. Likewise, processing strategies may include multiprocessing, multitasking, parallel processing, and the like. A program may be uploaded to, and executed by, the processor 102.

The processor 102 performs the workflows, data mining, model application, inverse treatment planning, and/or other processes described herein. For example, the processor 102 or a different processor is operable to extract values for the desired variables.

The processor 102 applies the values to a prognosis model relating a plurality of variables corresponding to the values to a probability of survival and/or complication. In one embodiment, each variable relates to a probability for outcome. The model parameters represent medical knowledge derived from literature. The probability as a function of the input values at a given dose or treatment region is determined. The probabilities for the values for the various variables are combined by the processor 102 for applying the model. The relationships may have been elicited from medical doctors.

The processor 102 applies the same values and/or additional values for the patient to another model in one embodiment. The other model is derived from a different knowledge base, such as being a statistical model derived from a database of patient data for a plurality of patients. The processor 102 may apply values to other models, such as another statistical model derived from a database. The variables used for the different models are the same or different, with or without overlap. The outputs of the various models are combined to provide probabilities of survival, complication, or other probabilities of a prognosis model.

The processor 102 outputs a chance of survival. The output may be a relationship of chance of survival to different doses for the given patient values. Similarly, a chance of side effects is output. The probabilities are part of dose distributions output by the processor or are individual probabilities independent of distribution. The output is internal to the processor 102 or output externally to the processor 102.

The input to an inverse treatment planning system is determined from one or more outputs of the prognosis model. The probabilities are used to determine dose to be input to the inverse treatment planning system. Alternatively, the probabilities, doses, tolerances, or other derived values are input to the inverse treatment planning system. For example, the probability of survival is used as a tumor control probability. The probability of survival may not be the same as the tumor control probability, but may be used in a similar manner. The probability of complications is used as a normal tissue complications probability. The probability of complications may not be the same as the normal tissue complications probability, but may be used in a similar manner. The probabilities and treatment goals are used to determine tumor and normal tissue dose and/or tolerances. The probabilities are associated with dosage.

The processor 102 or a different processor implements the inverse treatment planning system. Any now known or later developed inverse treatment planning system may be used. The inverse treatment planning system receives limitations, doses, goals, and/or other information and outputs treatment parameters for one or more radiation therapy systems to treat a tumor. The output parameters may provide a complete plan or a portion of a plan. Any now known or later developed parameters may be output.

The processor 102 may provide interaction between the prognosis model and the inverse treatment planning system. For example, the inverse treatment planning system outputs radiation treatment achievable doses, and the output of the prognosis model is used to determine possible probabilities given treatment goals and achievable dosage.

The processor 102 may determine a treatment regime, such as a treatment regime including radiation, surgery, and/or chemotherapy. The treatment regime may include radiation treatment. Achievable radiation treatment parameters are determined. A treatment regime is determined that satisfies the treatment goals with achievable radiation treatment parameters. One or more possible treatment regimes and associated probabilities may be output for user selection. In one embodiment, the optimum regime is determined to maximize and/or minimize probabilities based on selected or set priorities.

The processor 102 outputs the predicted outcome on the display 116, into a memory, over a network, to a printer, or in another media. The display 116 is a CRT, LCD, plasma, projector, monitor, printer, or other output device for showing data. The display is text, graphical, or other display.

The display 116 is operable to output radiation treatment parameters provided by the inverse treatment planning system as a function of one or more probabilities determined from a prognosis model. Other information may be output, such as the dose distributions, achievable doses, tumor dose, normal tissue dose, tolerances, treatment parameters, patient values, prognosis model information, inverse treatment planning information, combinations thereof, and/or other information. A probability of survival and/or a probability of complication may be output. Supporting information, such as values, different model outputs, options, or other supporting information, may be displayed.

The processor 102 operates pursuant to instructions. The instructions and/or patient record for automated treatment planning with individual specific consideration are stored in a computer readable memory, such as the external storage 114, ROM 106, and/or RAM 108. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

Figure 4:
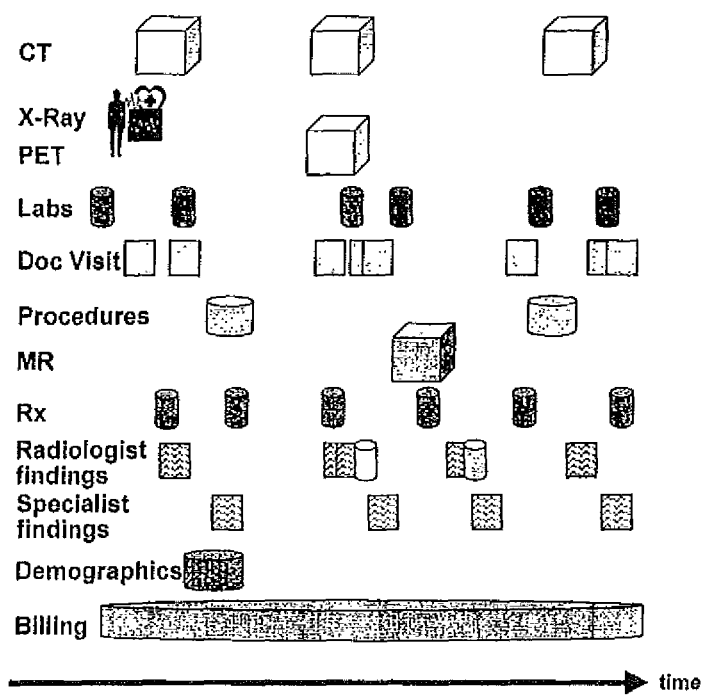
FIG. 4 is a graphical representation of a patient medical record in one example.

The same or different computer readable media may be used for the instructions, the individual patient record data, and the database of previously treated patients. The patient records are stored in the external storage 114, but may be in other memories. The external storage 114 may be implemented using a database management system (DBMS) managed by the processor 102 and residing on a memory, such as a hard disk, RAM, or removable media. Alternatively, the storage 114 is internal to the processor 102 (e.g. cache). The external storage 114 may be implemented on one or more additional computer systems. For example, the external storage 114 may include a data warehouse system residing on a separate computer system, a PACS system, or any other now known or later developed hospital, medical institution, medical office, testing facility, pharmacy or other medical patient record storage system. The external storage 114, an internal storage, other computer readable media, or combinations thereof store data for at least one patient record for a patient. The patient record data may be distributed among multiple storage devices as represented in FIG. 4 or in one location.

Increasingly, health care providers are employing automated techniques for information storage and retrieval. The use of a computerized patient record (CPR) to maintain patient information is one such example. As shown in FIG. 4, an exemplary CPR 200 includes information collected over the course of a patient's treatment or use of an institution. This information may include, for example, computed tomography (CT) images, X-ray images, laboratory test results, doctor progress notes, details about medical procedures, prescription drug information, radiological reports, other specialist reports, demographic information, family history, patient information, and billing (financial) information.

A CPR may include a plurality of data sources, each of which typically reflects a different aspect of a patient's care. Alternatively, the CPR is integrated into one data source. Structured data sources, such as financial, laboratory, and pharmacy databases, generally maintain patient information in database tables. Information may also be stored in unstructured data sources, such as, for example, free text, images, and waveforms. Often, key clinical findings are only stored within unstructured physician reports, annotations on images or other unstructured data source.

The database for deriving data driven models may be in the form of a CPR 200. Data for a plurality of patients having been previously treated are stored. Alternatively or additionally, the medical records for the individual to be treated are stored in the CPR 200.

In one embodiment, the patient values for application by the models, the data for a data-driven model development, and/or model parameters are mined from patient medical records. See U.S. Patent Application Publication No. 2003/0126101, the disclosure of which is incorporated herein by reference. Any now known or later developed data mining may be used. For structured medical records, different search routines may be used based on the structure. For unstructured or structured and unstructured medical records, probabilistic inference is used for mining in one embodiment. The mining is performed by a processor. For mining, facts are extracted from a patient record. The facts may be data points indicating a conclusion. The facts may or may not be accurate.

Patient records are mined for information related to a plurality of values corresponding to variables or possible variables used in modeling. In some situations, the patient record may be distributed or stored at different institutions. Different institutions include doctor's offices, hospitals, health care networks, clinics, imaging facility or other medical group. The different institutions have separate patient records, but may or may not be affiliated with each other or co-owned. In order to mine the patient records, the patient records from the different institutions are linked. As an example, consider a guideline from *The Specifications Manual for National Hospital Quality Measures*. If a patient is admitted to the hospital with a primary diagnosis of heart failure, then there should be documentation of left ventricular systolic function (LVSF) assessment at any time prior to arrival or during the hospitalization. First, the hospital records are searched to find patients who were admitted with a primary diagnosis of heart failure. This can be done by searching the records (e.g., billing records and/or other data sources) of a hospital. To assess the second part, however, is a little more complicated. If a mention of LVSF assessment exists in the hospital records, as part of the history, discharge summary, or somewhere else, then the data can be assessed from the hospital data alone. Often, however, the data is not available there, but elsewhere. For example, if the patient was referred to the hospital by his cardiologist, who performed the LVSF assessment in his office the previous day, then the record of LVSF assessment is with the physician in his practice notes. If the LVSF assessment was done at one hospital, and then the patient was transferred to the current hospital, then the record of the LVSF assessment is with the previous hospital.

The values for modeling or to be applied to a model are derived from the extracted information. The values are determined from one or more data points. The values may be derived as part of the extraction. For example, the values are derived probabilistically by combining factoids. The values may be derived from already extracted information. Non-probabilistic derivation may be used.

Example embodiments for data mining include mining from unstructured patient records using probabilities. U.S. Published Application No. 2003/0120458 discloses mining unstructured and structured information to extract structured clinical data. Missing, inconsistent or possibly incorrect information is dealt with through assignment of probability or inference. These mining techniques are used for quality adherence (U.S. Published Application No. 2003/0125985), compliance (U.S. Published Application No. 2003/0125984), clinical trial qualification (U.S. Published Application No. 2003/0130871), billing (U.S. Published Application No. 2004/0172297), projection of patient states (U.S. Published Application No. 2003/0126101), and improvements (U.S. Published Application No. 2006/0265253). The disclosures of these published applications referenced above are incorporated herein by reference. Other patient data mining or mining approaches may be used, such as mining from only structured information, mining without assignment of probability, or mining without inferring for inconsistent, missing or incorrect information.

Figure 5:
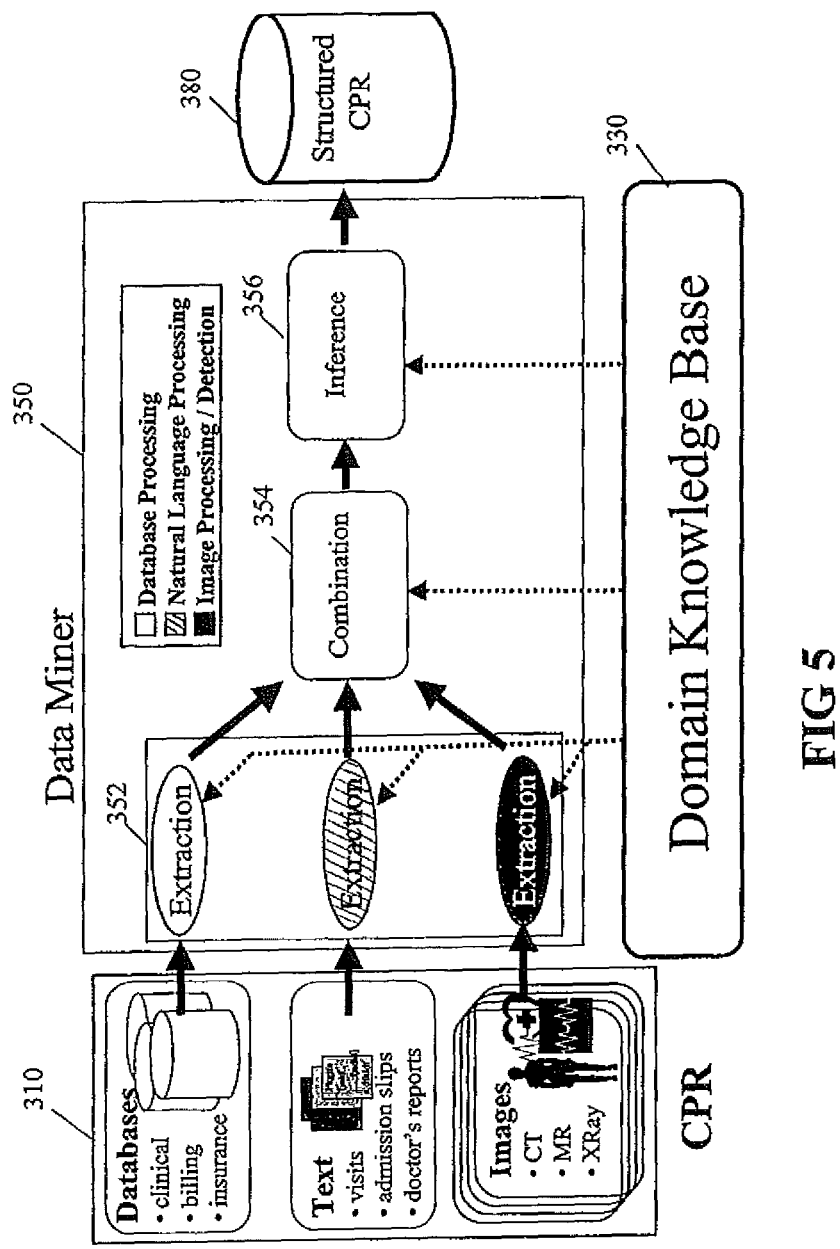
FIG. 5 is a graphical representation of one embodiment of a data miner for deriving individual patient input for a prognosis model.

The processor 102 or a different processor mines the patient records and automatically extracts values. FIG. 5 illustrates an exemplary data mining system implemented by the processor 102 for mining a patient record to create high-quality structured clinical information. The processing components of the data mining system are software, firmware, microcode, hardware, combinations thereof, or other processor based objects. The data mining system includes a data miner 350 that mines information from a computerized patient record (CPR) 310 using domain-specific knowledge contained in a knowledge base 330. The data miner 350 includes components for extracting information from the CPR 352, combining all available evidence in a principled fashion over time 354, and drawing inferences from this combination process 356. The mined information may be stored in a structured CPR 380. The architecture depicted in FIG. 5 supports plug-in modules wherein the system can be easily expanded for new data sources, diseases, and hospitals. New element extraction algorithms, element combining algorithms, and inference algorithms can be used to augment or replace existing algorithms.

The mining is performed as a function of domain knowledge. Detailed knowledge regarding the domain of interest, such as, for example, a disease of interest, guides the process to identify relevant information. This domain knowledge base 330 can come in two forms. It can be encoded as an input to the system, or as programs that produce information that can be understood by the system. For example, a clinical guideline to diagnosing a particular disease or diseases provides information relevant to the prognosis. The clinical guideline is used as domain knowledge for the mining. The domain knowledge may be provided from literature sources associated with prognosis. Additionally or alternatively, the domain knowledge base 330 may be learned from test data as a function or not as a function of an otherwise developed clinical guideline. The learned relationships of information to a diagnosis or prognosis may be a clinical guideline.

The domain-specific knowledge may also include disease-specific domain knowledge. For example, the disease-specific domain knowledge may include various factors that influence risk of a disease, disease progression information, complications information, outcomes, and variables related to a disease, measurements related to a disease, and policies and guidelines established by medical bodies. The domain-specific knowledge base may include synonyms, terms, or other indicators determined to be relevant to a particular condition, guideline, or influencing factors.

The information identified as relevant by the clinical guideline provides an indication of probability that a factor or item of information indicates or does not indicate a particular diagnosis or prognosis. The relevance may be estimated in general, such as providing relevance for any item of information more likely to indicate a diagnosis or prognosis as 75% or other probability above 50%. The relevance may be more specific, such as assigning a probability of the item of information indicating a particular prognosis based on clinical experience, literature, tests, studies or machine learning. The domain knowledge indicates elements with a probability greater than a threshold value of indicating the patient state, diagnosis, desired data point, value, prognosis, or measure. Other probabilities may be associated with combinations of information.

Domain-specific knowledge for mining the data sources may include institution-specific domain knowledge. For example, information about the data available at a particular hospital, document structures at a hospital, policies of a hospital, guidelines of a hospital, and any variations associated with a hospital. The domain knowledge guides the mining, but may guide without indicating a particular item of information from a patient record.

The extraction component 352 deals with gleaning small pieces of information from each data source regarding a patient or plurality of patients. The pieces of information or elements are represented as probabilistic assertions about the patient at a particular time. Alternatively, the elements are not associated with any probability. The extraction component 352 takes information from the CPR 310 to produce probabilistic assertions (elements) about the patient that are relevant to an instant in time or period. This process is carried out with the guidance of the domain knowledge that is contained in the domain knowledge base 330. The domain knowledge for extraction is generally specific to each source, but may be generalized.

The data sources include structured and/or unstructured information. Structured information may be converted into standardized units, where appropriate. Unstructured information may include ASCII text strings, image information in DICOM (Digital Imaging and Communication in Medicine) format, or text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge encodes what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images or waveforms may be carried out by image processing or feature extraction programs that are provided to the system. Extraction from a text source may be carried out by phrase spotting, which requires a list of rules that specify the phrases of interest and the inferences that can be drawn there from. For example, if there is a statement in a doctor's note with the words "there is evidence of metastatic cancer in the liver," then, in order to infer from this sentence that the patient has cancer, a rule directs the system to look for the phrase "metastatic cancer." If the phrase is found, an assertion that the patient has cancer with a high degree of confidence (which, in the present embodiment, translates to generate an element with name "Cancer", value "True" and confidence 0.9) is generated.

The combination component 354 combines all the elements that refer to the same variable at the same period to form one unified probabilistic assertion regarding that variable. Combination includes the process of producing a unified view of each variable at a given point in time from potentially conflicting assertions from the same/different sources. These unified probabilistic assertions are called factoids. The factoid is inferred from one or more elements. Where the different elements indicate different factoids or values for a factoid, the factoid with a sufficient (threshold) or highest probability from the probabilistic assertions is selected. The domain knowledge base may indicate the particular elements used. Alternatively, only elements with sufficient determinative probability are used. The elements with a probability greater than a threshold of indicating a patient state (e.g., directly or indirectly as a factoid), are selected. In various embodiments, the combination is performed using domain knowledge regarding the statistics of the variables represented by the elements ("prior probabilities").

The patient state is an individual model of the state of a patient. The patient state is a collection of variables that one may care about relating to the patient, such as established by the domain knowledgebase. The information of interest may include a state sequence, i.e., the value of the patient state at different points in time during the patient's treatment.

The inference component 356 deals with the combination of these factoids, at the same point in time and/or at different points in time, to produce a coherent and concise picture of the progression of the patient's state over time. This progression of the patient's state is called a state sequence. The patient state is inferred from the factoids or elements. The patient state or states with a sufficient (threshold), high probability or highest probability are selected as an inferred patient state or differential states.

Inference is the process of taking all the factoids and/or elements that are available about a patient and producing a composite view of the patient's progress through disease states, treatment protocols, laboratory tests, clinical action, or combinations thereof. Essentially, a patient's current state can be influenced by a previous state and any new composite observations.

The domain knowledge required for this process may be a statistical model that describes the general pattern of the evolution of the disease of interest across the entire patient population and the relationships between the patient's disease and the variables that may be observed (lab test results, doctor's notes, or other information). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability=0.9), cancer=unknown (probability=0.1)>).

Now, further assume that there is a base probability of cancer <cancer=True (probability=0.35), cancer=False (probability=0.65)> (e.g., 35% of patients have cancer). Then, this assertion is combined with the base probability of cancer to obtain, for example, the assertion <cancer=True (probability=0.93), cancer=False (probability=0.07)>.

Similarly, assume conflicting evidence indicated the following:

1. <cancer=True (probability=0.9), cancer=unknown probability=0.1)>
2. <cancer=False (probability=0.7), cancer=unknown (probability=0.3)>
3. <cancer=True (probability=0.1), cancer=unknown (probability=0.9)> and 4. <cancer=False (probability=0.4), cancer=unknown (probability=0.6)>.

In this case, these elements might be combined with the base probability of cancer <cancer=True (probability=0.35), cancer=False (probability=0.65)> to conclude, for example, that <cancer=True (prob=0.67), cancer=False (prob=0.33)>.

In alternative embodiments, specific probabilistic conclusions are determined without mining for an overall or temporal patient state. For example, the values for prognosis prediction are extracted without determining a progression of conditions or other history associated with a patient.

Numerous data sources may be assessed to gather the elements, and deal with missing, incorrect, and/or inconsistent information. As an example, consider that, in determining whether a patient has diabetes, the following information might be extracted:

(a) ICD-9 billing codes for secondary diagnoses associated with diabetes;

(b) drugs administered to the patient that are associated with the treatment of diabetes (e.g., insulin);

(c) patient's lab values that are diagnostic of diabetes (e.g., two successive blood sugar readings over 250 mg/d);

(d) doctor mentions that the patient is a diabetic in the H&P (history & physical) or discharge note (free text); and (e) patient procedures (e.g., foot exam) associated with being a diabetic.

As can be seen, there are multiple independent sources of information, observations from which can support (with varying degrees of certainty) that the patient is diabetic (or more generally has some disease/condition). Not all of them may be present, and in fact, in some cases, they may contradict each other. Probabilistic observations can be derived, with varying degrees of confidence. These observations (e.g., about the billing codes, the drugs, the lab tests, etc.) may be probabilistically combined to come up with a final probability of diabetes. Note that there may be information in the patient record that contradicts diabetes. For instance, the patient has some stressful episode (e.g., an operation) and his blood sugar does not go up. In another example, observations of ST-elevations in an EKG can increase confidence that the patient had a heart attack, even though the ST-elevations alone are not conclusive evidence of a heart attack.

The above examples are presented for illustrative purposes only and are not meant to be limiting. The actual manner in which elements are combined depends on the particular domain under consideration as well as the needs of the users of the system. Further, while the above discussion refers to a patient-centered approach, multiple patients may be handled simultaneously. Additionally, a learning process may be incorporated into the domain knowledge base 330 for any or all of the stages (i.e., extraction, combination, inference).

In the case of missing information, no supporting evidence is found. The processor 102 may respond in one of two ways. The field may be left blank, or a prior probability is used to compute the most likely response. For example, one of the questions asked is whether the patient is a smoker or not. If there is no evidence provided in the patient record if the user is a smoker, then the system leaves this blank or records that the user is not a smoker, since the prior probability (based on the percentage of smokers) suggests that the patient is probably not a smoker.

The mining may be run using the Internet. The created structured clinical information may also be accessed using the Internet. Additionally, the data miner may be run as a service. For example, several hospitals may participate in the service to have their patient information mined for compliance, and this information may be stored in a data warehouse owned by the service provider. The service may be performed by a third party service provider (i.e., an entity not associated with the hospitals).

The domain knowledgebase, extractions, combinations and/or inference may be responsive or performed as a function of one or more parameter values. For example, the probabilistic assertions may ordinarily be associated with an average or mean value. However, some medical practitioners or institutions may desire that a particular element be more or less indicative of a patient state. A different probability may be associated with an element. As another example, the group of elements included in the domain knowledge base for a particular disease or clinical guideline may be different for different people or situations. The threshold for sufficiency of probability or other thresholds may be different for different people or situations.

The mining generates data points and/or values. Once the structured CPR 380 is populated with patient information, data points are provided in a form conducive for answering questions regarding prognosis, such as determining values for modeled predictors or variables. The structured information may include the values in addition to data points used to derive the values. For example, the factoids and the combined information are included as extracted or structured information.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for automated treatment planning with individual specific consideration, the system comprising:
    an input operable to receive values for a plurality of patient specific characteristics of a patient;
    a processor configured to apply the received values to a first prognosis model, the first prognosis model relating a plurality of variables corresponding to values to a first probability at a given dose, the processor configured to provide a first input for treatment planning, the first input being a function of the first probability; and
    a display operable to output treatment parameters provided by the treatment planning as a function of the first probability;
    wherein the first prognosis model relates the variables to the first probability as a function of medical knowledge from literature.

2. The system of claim 1 wherein the input comprises a data interface operable to receive values mined from data by the processor or a different processor.

3. The system of claim 1 wherein the first prognosis model is a function of the medical knowledge collected from the literature converted into a functional relationship for each variable independent of other variables.

4. The system of claim 1 wherein the processor is configured to apply the received values or additional values of the patient to a second prognosis model, the second prognosis model being a statistical model derived from a database of patient data for a plurality of patients, the first probability being a function of outputs of the first and second prognosis models.

5. The system of claim 1 wherein the first prognosis model is configured to output a chance of survival as the first probability, wherein the chance of survival input to the treatment planning is a tumor control probability.

6. The system of claim 5 wherein the first prognosis model is configured to output a chance of side effect as a second probability, wherein the chance of side effect input to the treatment planning is a normal tissue complications probability.

7. The system of claim 1 wherein the first prognosis model is configured to output a chance of side effect as the first probability, wherein the chance of side effect input to the treatment planning is a normal tissue complications probability.

8. The system of claim 1 wherein the first prognosis model is configured to output a dose distribution as a function of the values, the dose distribution including the first probability at the given dose, the first input being the dose distribution.

9. The system of claim 8 wherein the dose distribution is for chemotherapy.

10. The system of claim 8 wherein the dose distribution is for a drug.

11. The system of claim 1 wherein the processor is configured to provide interaction between the first prognosis model and the treatment planning, the first prognosis model configured to determine a second probability as a function of at least one of the output treatment parameters.

12. The system of claim 11 wherein the processor is configured to determine a treatment regime, the treatment regime being a function of achievable treatment parameters.

13. A non-transitory computer readable storage medium having stored therein data representing instructions configured for execution by a programmed processor for automated treatment planning with individual specific consideration, the instructions comprising:
    determining a first dose distribution of chance of survival as a function of a dose, wherein the first dose distribution output by a prognosis model is a function of first values specific to an individual patient;
    determining a second dose distribution of chance of complication as a function of dose, wherein the second dose distribution output by the prognosis model is a function of second values specific to the individual patient;
    selecting a dose from the first dose distribution corresponding to a desired chance of survival;
    selecting a dose tolerance from the second dose distribution corresponding to a desired chance of complication; and
    determining a treatment plan as a function of the dose and the dose tolerance;
    wherein selecting the dose and the dose tolerance comprise relating the first dose distribution to the second dose distribution.

14. The non-transitory computer readable storage medium of claim 13 wherein the instruction of determining the first and second dose distribution comprise determining with the prognosis model having a knowledge base from clinical study publications.

15. The non-transitory computer readable storage medium of claim 13 wherein the instructions further comprise:
    optimizing the dose and the dose tolerance as a function of feedback from an inverse treatment planning system, the inverse treatment planning system configured to output the treatment plan.

16. The non-transitory computer readable storage medium of claim 13 wherein the instruction of selecting the dose from the first dose distribution corresponds to the desired chance of complication.

17. A method for automated treatment planning with individual specific consideration, the method comprising:
    applying, by a processor, patient specific values to a prognostic model;
    outputting, by the processor, a probability of survival from the prognostic model in response to the applying;
    inputting a first dose, for treatment planning, the first dose being a function of the probability of survival; and
    providing a treatment plan in response to the inputting of the first dose;
    wherein outputting comprises estimating, by the processor, with the prognostic model, the prognostic model representing a plurality of different types of sources of knowledge base;
    wherein outputting the probability of survival comprises estimating a first dose distribution of probability of survival as a function of dose;
    further comprising:
    estimating, with the prognostic model in response to the applying, a second dose distribution of probability of complication as a function of dose; and
    selecting the first dose as a function of the first and second dose distributions.

18. The method of claim 17 further comprising:
    feeding back an achievable tumor dose and an achievable tolerance dose from the treatment planning; and
    optimizing the treatment plan as a function of the achievable tumor dose, the achievable tolerance dose, and the first and second dose distributions.

19. The method of claim 17 further comprising: selecting a treatment regime with the prognostic model as a function of the values.

20. The method of claim 17 wherein outputting the probability of survival comprises outputting a probability of survival from cancer.

21. A method for automated treatment planning with individual specific consideration, the method comprising:
    applying, by a processor, patient specific values to a prognostic model;
    outputting, by the processor, a probability of survival from the prognostic model in response to the applying;
    inputting a first dose for treatment planning, the first dose being a function of the probability of survival; and
    providing a treatment plan in response to the inputting of the first dose;
    wherein outputting comprises estimating, by the processor, with the prognostic model, the prognostic model representing a plurality of different types of sources of knowledge base;
    further comprising:
    outputting a probability of complications from the prognostic model in response to the applying; and
    selecting the first dose as a tumor dose and selecting a tolerance dose, the tumor dose and tolerance dose each being a function of the probability of survival and the probability of complications; and
    inputting the tolerance dose in accordance to the treatment planning.

22. A system for automated treatment planning with individual specific consideration, the system comprising:
    an input operable to receive values for a plurality of patient specific characteristics of a patient;
    a processor configured to apply the received values to a first prognosis model, the first prognosis model relating a plurality of variables corresponding to values to a first probability at a given dose, the processor configured to provide a first input to a treatment planning system, the first input being a function of the first probability; and a display operable to output treatment parameters provided by the treatment planning system as a function of the first probability;

wherein the first prognosis model relates the variables to the first probability as a function of medical knowledge from literature.

* * * * *